(12) United States Patent
Tegge et al.

(10) Patent No.: US 6,252,042 B1
(45) Date of Patent: Jun. 26, 2001

(54) COMPOUNDS FOR DETECTING PHOSPHORIC ACID ESTERS

(75) Inventors: Werner Tegge; Rainer Gast; Joern Gloekler, all of Braunschweig (DE)

(73) Assignee: Gesellschaft fuer Biotechnologische Forschung mbH (GBF), Braunschweig (DE)

( * ) Notice: Subject to any disclaimer, the term of this patent is extended or adjusted under 35 U.S.C. 154(b) by 0 days.

(21) Appl. No.: 09/381,387

(22) PCT Filed: Mar. 23, 1998

(86) PCT No.: PCT/EP98/01689

§ 371 Date: Jan. 18, 2000

§ 102(e) Date: Jan. 18, 2000

(87) PCT Pub. No.: WO98/43082

PCT Pub. Date: Oct. 1, 1998

(30) Foreign Application Priority Data

Mar. 21, 1997 (DE) ............................... 197 11 796

(51) Int. Cl.⁷ ........................ A61K 38/00; C07D 413/00; C07D 403/00; C07D 263/34; C07D 209/04

(52) U.S. Cl. ........................ 530/345; 544/369; 544/373; 548/236; 548/511

(58) Field of Search .............................. 530/345; 544/369, 544/373; 548/236, 511

(56) References Cited

FOREIGN PATENT DOCUMENTS

WO9730074 * 8/1997 (WO).

OTHER PUBLICATIONS

Yuan et al., "Synthesis of a new tetradentate beta–diketonate–europium chelate that can be covalently bound to proteins in time–resolved fluorometry," Anal. Sci., 1996, vol. 12, No. 5, pp. 695–699.*

* cited by examiner

*Primary Examiner*—John S. Brusca
*Assistant Examiner*—Young Kim
(74) *Attorney, Agent, or Firm*—Pitney, Hardin, Kipp & Szuch, LLP

(57) ABSTRACT

Complexes, especially for the detection and separation of phosphoric-ester-containing compounds, are disclosed. The complexes according to the invention comprise at least one chelating agent, at least one central atom or central ion coordinated by the chelating agent(s), and at least one dye bonded to the chelating agent(s), etc.

15 Claims, 5 Drawing Sheets

Sequence:

| | 1 | 2 | 3 | 4 | 5 | 6 | 7 | 8 | 9 | 10 | |
|---|---|---|---|---|---|---|---|---|---|---|---|
| R3 | A | H | R | A | S | A | A | - | - | - | pmol |
| | 39 | 9 | 21 | 30 | 5 | 20 | 19 | | | | |
| | inter | R | | | | | | | | | |
| | alia | 11 | | | | | | | | | |

| 11 | 12 | 13 | 14 | 15 | 16 | 17 | 18 | 19 | 20 | |
|---|---|---|---|---|---|---|---|---|---|---|
| | | | | | | | | | | pmol |

Sequence:

| | 1 | 2 | 3 | 4 | 5 | 6 | 7 | 8 | 9 | 10 | |
|---|---|---|---|---|---|---|---|---|---|---|---|
| R2 | A | R | R | A | S | A | A | - | - | - | pmol |
| | 18 | 11 | 10 | +10 | 2.4 | +2.5 | +1.6 | | | | |
| | inter | | | | | | | | | | |
| | alia | | | | | | | | | | |

| 11 | 12 | 13 | 14 | 15 | 16 | 17 | 18 | 19 | 20 | |
|---|---|---|---|---|---|---|---|---|---|---|
| | | | | | | | | | | pmol |

FIG. 4

COMPOUNDS FOR DETECTING PHOSPHORIC ACID ESTERS

The present invention relates to complexes (markers) especially for the detection of phosphoric esters, the complexes comprising a chelating agent, a central atom and a fluorescent dye.

Phosphoric esters are vital components of biological systems and are constituents of a large number of biochemical compounds. They play an important role in particular in the functioning and the regulation of cellular processes, occurring, for example, as intermediates in a large number of metabolic processes. Biologically important phosphoric esters include, for example, adenosine mono-, di- and tri-phosphates, lecithins, cephalins, phospholipids, nucleotides and co-enzymes. An especially large part in regulatory processes is also played by the phosphorylation and dephosphorylation of proteins by proteinkinases and phosphatases, respectively. The detection of phosphorylated molecules, that is to say the analysis of the phosphorylation state of biomolecules, is accordingly of considerable importance in biological research.

The radioactive labelling of phosphorylated compounds with $^{32}P$ or $^{33}P$ and the detection of corresponding radionuclides is already known, but such procedures have the disadvantage that they require extensive safety precautions.

It is also known to use specific antibodies to detect phosphorylated compounds. The preparation of antibodies is complex, however, and therefore expensive, and their specificity is strongly influenced by structures other than the phosphate esters to be analysed. There therefore continues to be a need for alternative compounds for the detection of phosphoric esters.

The object of the present invention is accordingly to provide complexes that can be used for a very sensitive, non-hazardous and specific assay, such as, for example, the detection of phosphoric esters, or for the separation of compounds, such as proteins or peptides, without the need to use radionuclides or antibodies.

The object is achieved by a complex that comprises
a) at least one chelating agent,
b) at least one central atom or central ion coordinated by the chelating agent(s), and
c) at least one dye bonded to the chelating agent(s).

Preference is given to the use of multidentate chelating agents, such as iminodiacetic acid (IDA) and derivatives thereof, nitrilotriacetic acid and derivatives thereof, polyoxycarboxylic acids and derivatives thereof, polyamines and derivatives thereof, and ethylenediamineacetic acid and derivatives thereof.

The selective binding of IDA to phosphate esters by way of $Fe^{3+}$-chelation is already known, see Anderegg, G. & Schwarzenbach, G. (1955) Helv. Chim. Acta 38, 1940–1942; Muszynska, G. et al. (1992) J. Chromat. 604, 19–28; Schwarzenbach, G. et al. (1955) Helv. Chim. Acta 38, 1147–1170; Songyang, Z., Blechner, S., Hoagland, N., Hoekstra, M. F., Piwnica-Worms, H. & Cantley, L. C. (1994), Current Biology 4, 973–981. Also known is the use of immobilised IDA for the affinity purification or concentration of biomolecules on chromatography supports and membranes: for example, such a chelating chromatography material is marketed by the company Pharmacia Biotech under the name Chelating Superose/Sepharose.

A protein purification system is furthermore marketed by the company QIAGEN. That system can be used to isolate proteins and peptides that have been labelled with six consecutive histidine residues. Such residues have a high affinity for immobilised nickel ions, which in turn have been bound to nitrilotriacetic acid resins (Ni-NTA) by chelation. A considerable disadvantage of such a system, however, is the need to label the proteins and peptides with the histidine residues.

Also marketed by QIAGEN are conjugates of Ni-NTA with antibodies, peroxidase, alkaline phosphatase or horseradish peroxidase.

The use of the chelating effect in assays, however, especially for the direct detection and/or the separation of phosphate esters by means of a complex of a chelating agent with a dye (chromophore), is not known.

BRIEF DESCRIPTION OF THE DRAWINGS

FIG. 4 is a tabulation of the pool sequence analysis of the two group of beads, R2 and R3 which were sorted out of the population, as shown in FIG. 3.

According to the invention the central atom or central ion, of which there is at least one, preferably a metal atom or ion, especially a transition metal atom or ion, such as iron and/or nickel, coordinated by the chelating agent, can alternatively be one (or more) other group(s) that has (have) lone pairs of electrons or electron gaps. Preferably, $Fe^{3+}$ is used.

When several central atoms or ions are used, the complexes according to the invention may include one or more bridging ligands.

The dyes used in accordance with the invention are preferably bonded to the chelating agent chemically, but can be associated with the chelating agent in a different manner. The term "dyes" used here includes, in addition to conventional dyes, also pigments and other chromophore groups and starting materials therefor, which do not become chromophores, for example, until after reaction with the chelating agent(s). The dyes used may be, for example, xanthene dyes, such as fluorescent dyes, especially fluorescein and salts and derivatives thereof, such as fluorescein isothiocyanate.

A preferred compound according to the invention is the iron(III) complex of N-iminodiacetic acid ethyl N'-fluoresceinyl thiourea.

The compounds according to the invention can be prepared by a process in which at least one of the above-mentioned chelating agents is reacted under suitable conditions with at least one of the above-mentioned dyes and then at least one of the above-defined central atoms or ions is added under suitable conditions.

A preferred embodiment of the process according to the invention is illustrated in the following scheme: an aminoethyliminodiacetic acid (1) is reacted with fluorescein isothiocyanate (2) to form the compound (3). The chelate (4), that is to say a complex according to the present invention, can be precipitated after treatment with FeCl$_3$.

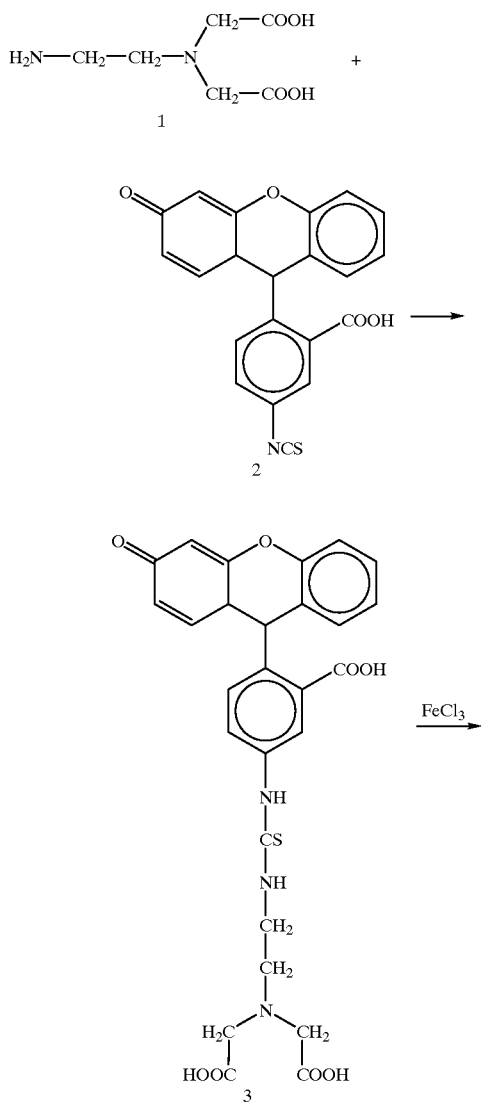

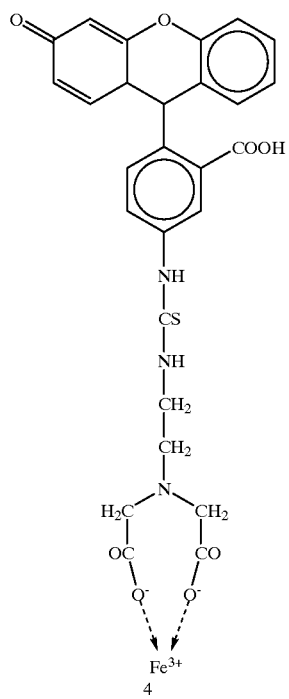

The complexes according to the invention can be used in an assay, preferably for the detection and/or separation of compounds of which at least some contain phosphoric ester groups. The following variations are possible:

Proteins or peptides that have identical or almost identical sequences can be analysed and separated (including physically separated) where the peptides or proteins or groups thereof have different numbers of phosphoric ester groups. The expression "almost identical sequences" in this context means preferably that the sequences differ by no more than one amino acid per 20 amino acids, especially per 30 amino acids, more especially per 40 amino acids and even more especially per 100 amino acids in the total frequency.

Figure 7:
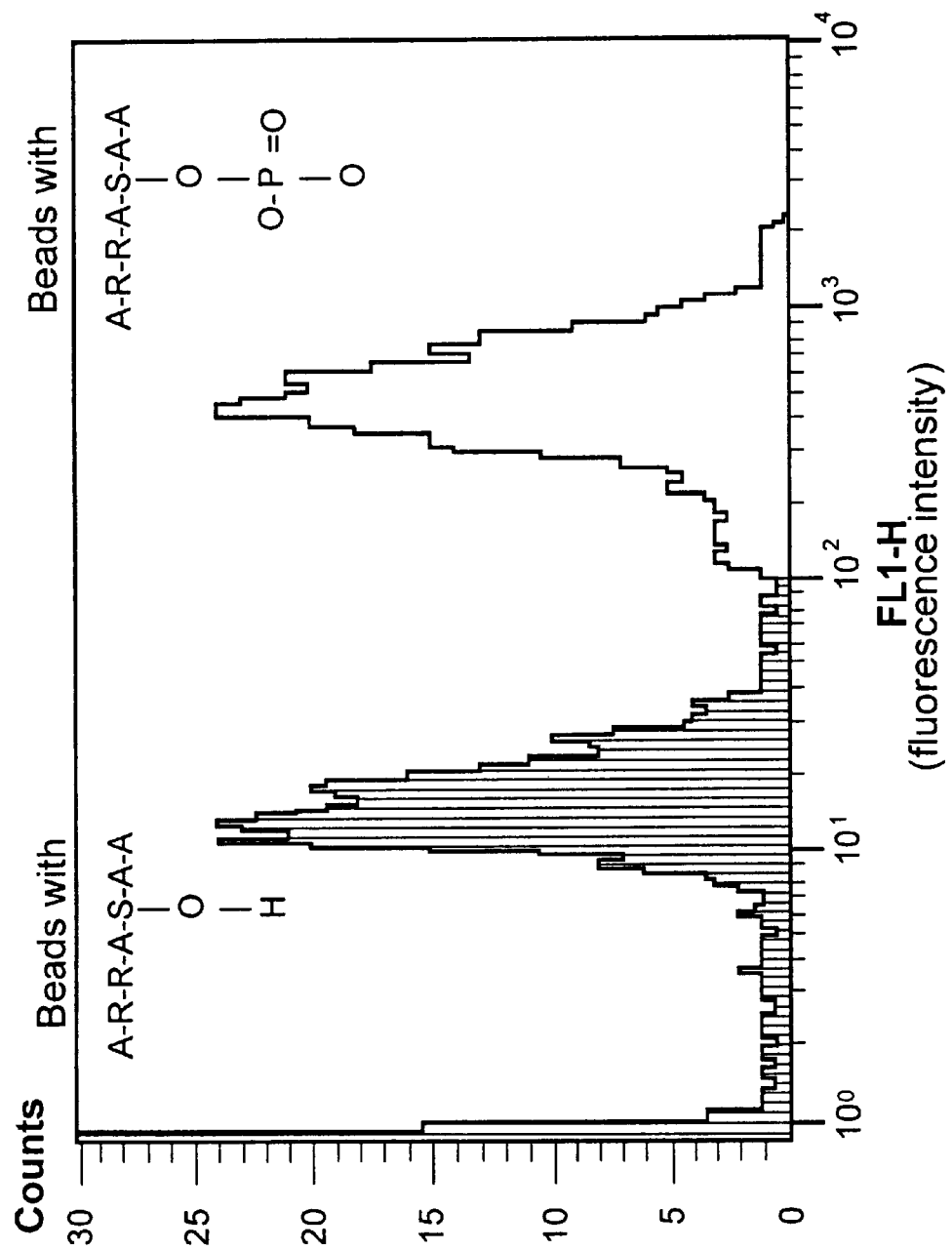
FIG. 7 if a graph of a FACS analysis sowing the difference in fluorescence between two populations of beads carrying an octapepide, one population having a serine phosphate and the other an umodified serine, following treatment with IDA and fluorescein as per the invention.

The analysis and/or separation of, for example, proteins or peptides that differ only in the number of phosphoric ester groups they contain is accordingly possible. A possible procedure therefor is as follows:

For example, two sorts of beads each carrying an octapeptide sequence were produced, the only difference between them being that one sequence contained a serine phosphate and the other an unmodified serine. After incubation of the beads with the above-mentioned IDA derivative (4), the two populations were examined by carrying out measurements in an FACS apparatus (cell scanner and sorter). The result is illustrated in the FIG. 7, which shows that the fluorescent labelling of the sequence containing the serine phosphate is significantly more intense; the two sorts of beads are separated nearly to the base line. Also possible is the analysis and/or separation (including physical separation) of proteins or peptides that differ from one another both in respect of the number of phosphoric ester groups they contain and in respect of their sequences. A possible procedure therefor is as follows:

Two sorts of agarose beads (20–40 μm diameter) with the bound heptapeptide sequences X-X-X-X-S-A-A (in which X=equal quantities of phenylalanine, tyrosine and tryptophan; S=serine, non-phosphorylated), and A-A-R-R-S(P)-

Figure 1:
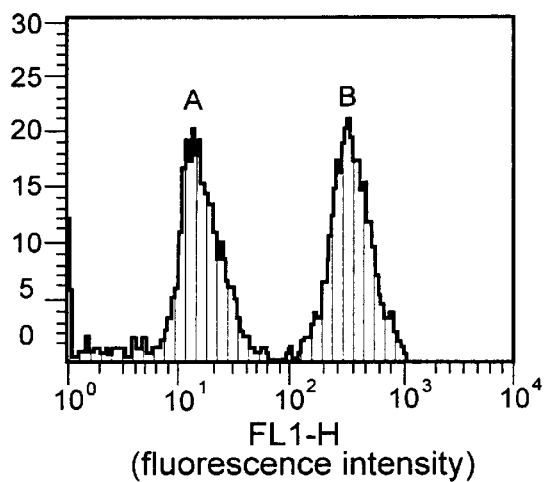
FIG. 1 is a graph of a FACS analysis showing the difference in fluorescence between two populations of agarose beads containing phosphorylated and non-phosphorylated sequences.

A-A (in which S(P)=phosphorylated serine, after incubation of the beads with PKA) were mixed in a ratio of 1:1 and, after treatment with a complex according to the invention, examined in a FACS apparatus. FIG. 1 shows the populations of phosphorylated (B) and non-phosphorylated (A) sequences of the two sorts of beads. The abscissa indicates the fluorescence intensities. Clear differentiation of the two populations and physical sorting in cell sorters are possible.

It is also possible to analyse and/or separate (including separate physically) proteins or peptides that have an identical or similar number of phosphoric ester groups but have other differences, such as different peptide or protein sequences. The physical sorting (separation) can be carried out in cell sorters.

The expression "a similar number of phosphoric ester groups" means preferably that the numbers of phosphoric ester groups in the different peptides or proteins differ by a maximum of 10%, preferably by a maximum of 5%, especially by a maximum of 2% and more especially by less than 1%, based on the number of phosphoric ester groups in the compound having the most phosphoric ester groups, the difference being at least one phosphoric ester group.

The expression "different sequences" means preferably that the sequences differ by at least 1 amino acid per 19 amino acids in the total sequence.

A possible procedure for the above process is as follows:

Beads having the corresponding non-phosphorylated sequences (e.g. X-X-X-X-S-A-A and A-A-R-R-S-A-A) are mixed and incubated with PKA (proteinkinase) and phosphorylated.

Figure 2:
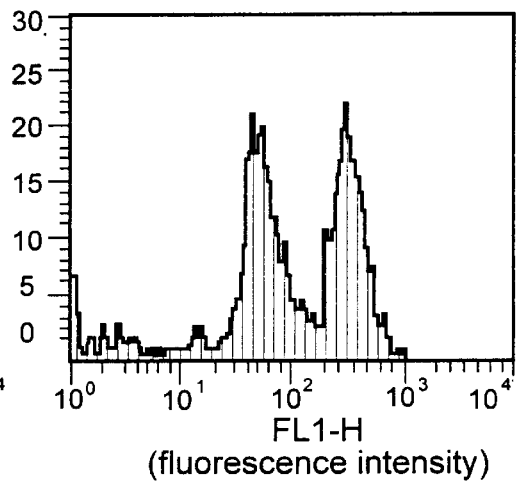
FIG. 2 is a graph of a FACS analysis showing the difference in fluorescence between two populations of agarose beads which were mixed and then treated with proteinkinase (PKA) and phosphorylated.

After treatment with a complex according to the invention, the result according to FIG. 2 was obtained. A clear and distinct separation of the two populations occurred, enabling physical sorting to be carried out in cell sorters.

Figure 3:
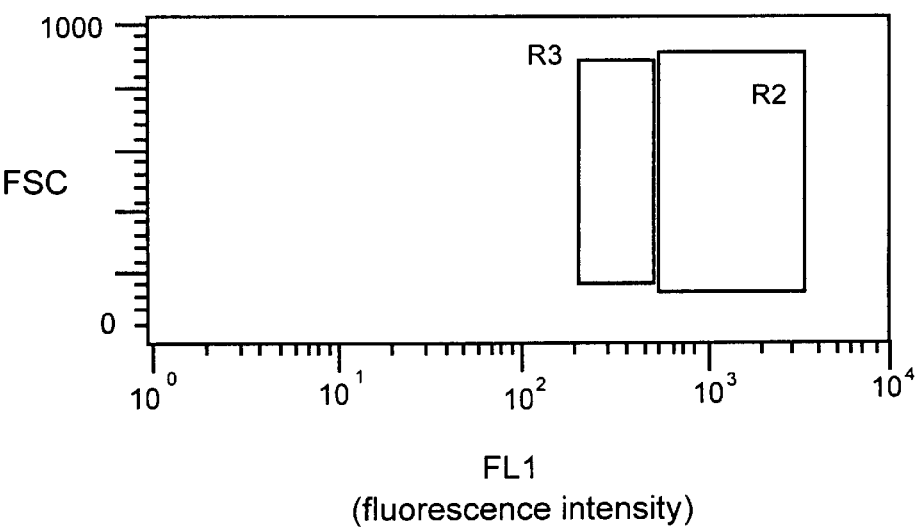
FIG. 3 is a FACS population distribution graph showing the two populations of beads, R2 and R3, which were sorted out by the FACS for further analysis.

In a further example, beads with the synthetically produced peptide library A-X-X-A-S-A-A (X=all natural amino acids, exc. Cys) are incubated with PKA and then treated with a complex according to the invention. The beads with the highest fluorescence were selected using a FACS sorter (two populations, R2 and R3, according to FIG. 3). The pool sequence analysis of the collected beads (FIG. 4) shows that the beads carry mainly arginine (R) in the X positions, which corresponds to the known recognition motif of that proteinkinase.

The procedure is therefore suitable for the identification of consensus motifs of a large number of, for example, identified but little characterised proteinkinases.

The complexes according to the invention can also be used in many other assays, such as, for example, in the analysis and separation of phosphoric-ester-group-containing proteins and peptides in protein gels or on blots, in capillary electrophoresis and gel electrophoresis.

Capillary Electrophoresis

Figure 5:
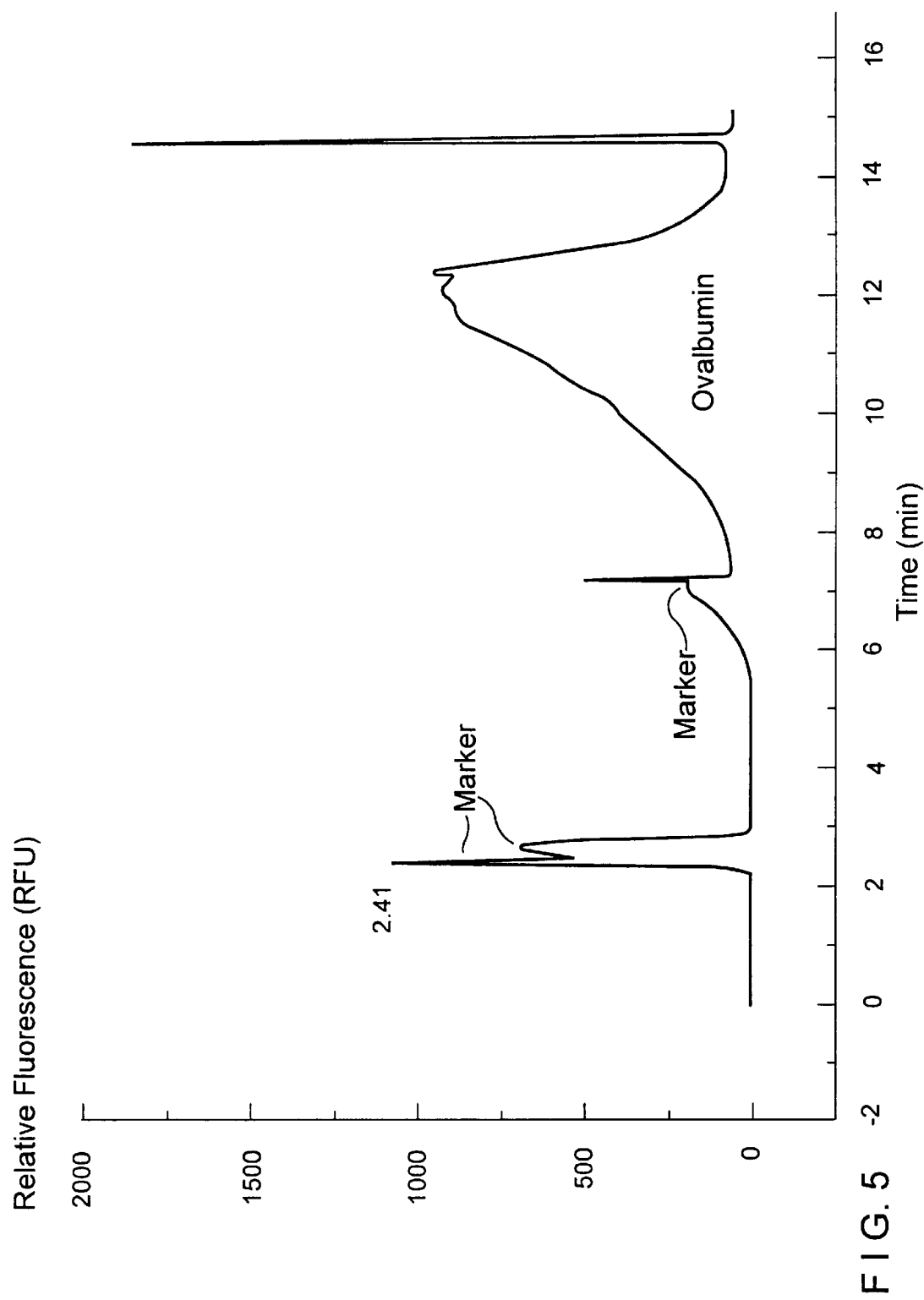
FIG. 5 is a graph of the fluorescence of ovalbumin which was labeled with fluorescein/IDA/iron complex according to the invention and then separated by capillary electrophoresis.
Figure 6:
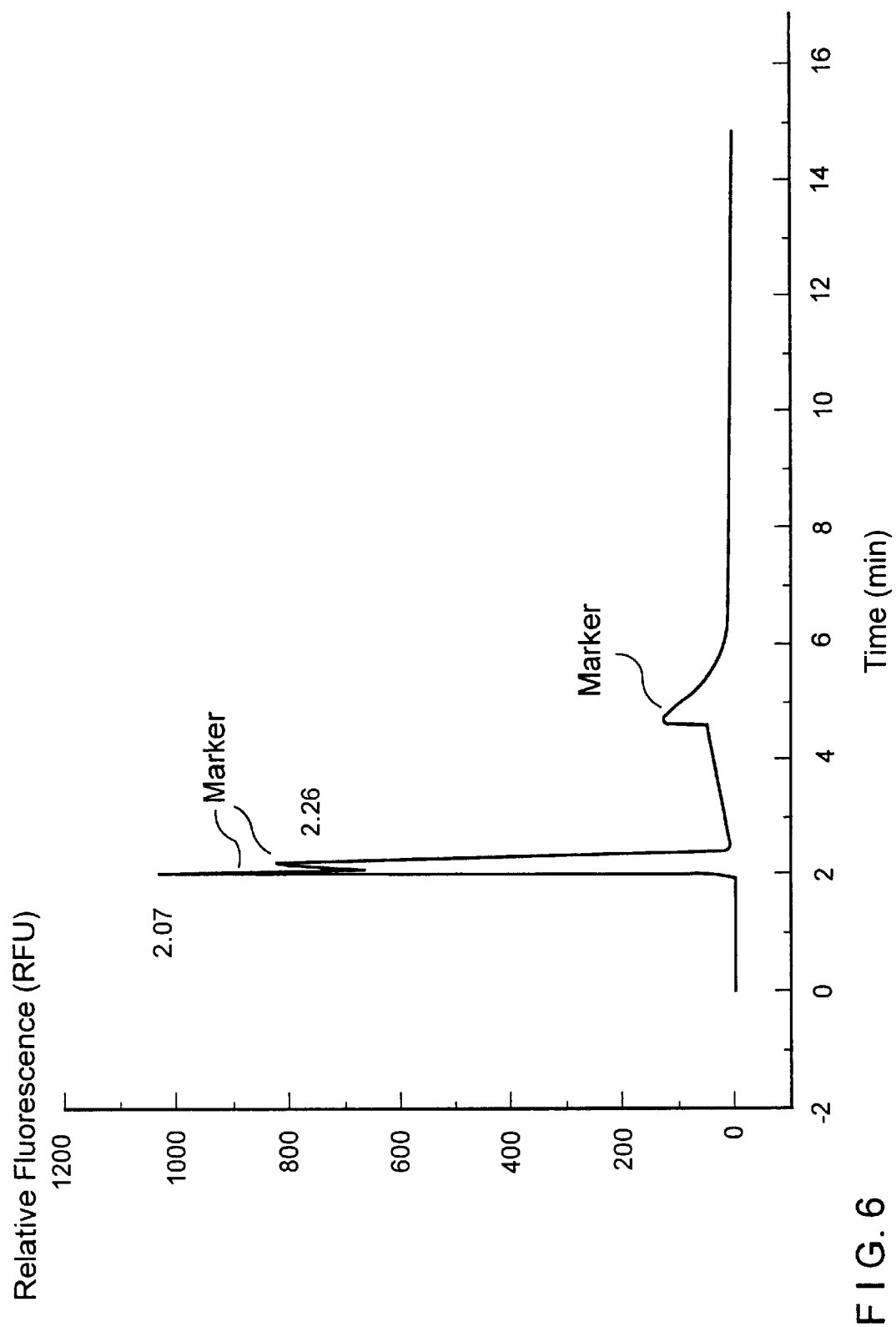
FIG. 6 is a graph of the fluorescence of the control protein, glucose oxidase, which was similarly labeled as the ovalbumin in FIG. 5, and then separated by capillary electophoresis.

In separation using a capillary electrophoresis system, ovalbumin, as a phosphorylated protein, became intensely labelled with the fluorescein/IDA/iron complex according to the invention and was detected using an appropriate detector (FIG. 5). The non-phosphorylated control protein glucose oxidase exhibited only a weak background fluorescence (FIG. 6).

This field of use allows the efficient monitoring of biological phosphorylation processes in in vitro and in vivo assays.

Protein Blots

Proteins can be separated by gel electrophoresis. The individual proteins can then be blotted onto a support membrane. Phosphorylated proteins were specifically labelled with the fluorescein/IDA/iron complex on such blots (nitrocellulose).

Finally, the complexes according to the invention can be used for the detection of recombinant peptides or proteins having His tags (e.g. an additional sequence of 6 histidine residues), it being possible to use as central atom or ion transition metals other than Fe, such as, for example, Cu, Ni, Co and/or Zn atoms or ions.

To summarize, the present invention enables, for example, proteins and peptides to be quantified and separated in a simple manner because a stoichiometric, time-stable quantification of the fluorescent group is effected. A further advantage resides in the reversible nature of the staining, it being possible for the staining to be reversed by the addition of strong chelating agents (EDTA) or by alteration of the pH.

EXAMPLES

Preparation of N-ethoxycarbonylethylenediamine 15 g (0.13 mol) of diethyl carbonate are heated in an oil bath at 90° C., for five hours, with 10 g (0.17 mol) of ethylenediamine under reflux. The ethyl alcohol formed during the reacton is then removed using a rotary evaporator. The product is removed from the residue by distillation in a Kugelrohr distillation apparatus.

Transition: 160° C. (4 mbar)

Yield: 8.5 g (50% of theory)

Preparation of N-ethoxycarbonyl-β-aminoethyliminodiacetic acid dimethyl ester 8.5 g (64 mmol) of N-ethoxycarbonylethylenediamine, 8.85 g (64 mmol) of potassium carbonate and 19.58 g (128 mmol) of methyl bromoacetate are combined in that order. A vigorous reaction occurs, and after it has subsided the mixture is heated under reflux for four hours in an oil bath at 95° C. After approximately ½ hour, the evolution of $CO_2$ commences and shortly afterwards subsides again. At the end of the reaction time the residue is extracted by boiling in 100 ml of diethyl ether, the ether is removed using a rotary evaporator and the ester is distilled of in a Kugelrohr distillation apparatus.

Transition: 220° C. (0.1 mbar)

Yield: 10.12 g (57% of theory)

Preparation of Aminoethyliminodiacetic Acid (IDA, 1)

10.12 g (37 mmol) of N-ethoxycarbonyl-β-aminoethyliminodiacetic acid dimethyl ester are added to 650 ml of a 0.15 molar barium hydroxide solution. The mixture is heated under reflux at 95° C. for two hours in an oil bath. After cooling, 9.95 g of a 95–97% sulphuric acid are added dropwise with vigorous stirring. The suspension is then centrifuged and concentrated using a rotary evaporator. The pure product is obtained by recrystallisation from water/ethanol.

Yield: 4.00 g (61% of theory)

Preparation of N-iminodiacetic acid ethyl N'-fluoresceinyl Thiourea (3)

50 mg (0.28 mmol) of aminoethyliminodiacetic acid are dissolved in 5 ml of water. The solution is then adjusted to pH 10.5 with a 0.2M sodium hydroxide solution. 3 ml of an ethanolic fluorescein isothiocyanate suspension (corresponding to 120 mg (0.30 mmol) of FITC) are added thereto using a pipette. The pH should not go beyond 8 and is corrected to the initial value again in alternation with the addition of the suspension.

Once the addition is complete, the pH correction is carried out hourly for approximately five more hours. The mixture is then stirred for 48 hours at room temperature with the exclusion of light, and during that time is repeatedly readjusted to pH 10.5. Towards the end of the reaction the pH remains stable. The solution is subsequently adjusted to pH 2.5 using 1M HCl, the product precipitating. The product is washed in 5 ml of ethanol and dried in vacuo.

Yield: 100 mg (66.6% of theory)

Preparation of the Iron(III) Complex of the IDA Derivative (4)

20 mg (0.035 mmol) of N-iminodiacetic acid ethyl N'-fluoresceinyl thiourea are dissolved in 5 ml of water and the solution is adjusted to pH 7.0 using sodium hydroxide solution. A solution consisting of 10 mg (0.037 mmol) of $FeCl_3 \times 6\ H_2O$ in 5 ml of water is then added, a black solid immediately being precipitated; the precipitate is isolated by filtration and subsequently washed with 5 ml of water.

Yield: 20 mg

What is claimed is:

1. A method for labeling peptides or proteins that contain phosphoric ester groups comprising treating the peptides or proteins to be labeled with a complex that comprises:
    a) at least one chelating agent;
    b) at least one central atom or central ion bonded to said at least one chelating agent; and
    c) at least one dye bonded to said at least one chelating agent.
2. The method according to claim 1, wherein said at least one chelating agent is a multidentate chelating agent.
3. The method according to claim 2, wherein said multidentate chelating agent is selected from the group consisting of iminodiacetic acid or derivatives thereof, nitrilotriacetic acid or derivatives thereof, polyoxycarboxylic acids or derivatives thereof, polyamines or derivatives thereof, and ethylenediamineacetic acid or derivatives thereof.
4. The method according to claim 1, wherein said at least one central atom or central ion is at least one metal atom or ion.
5. The method according to claim 4, wherein said metal atom or ion is at least one transition metal atom or ion.
6. The method according to claim 5, wherein said transition metal or ion is $Fe^{3+}$.
7. The method according to claim 1, wherein said at least one dye is a xanthene dye.
8. The method according to claim 7, wherein said xanthene dye is a fluorescent dye.
9. The method according to clam 8, wherein said fluorescent dye has a fluorescein residue.
10. The method according to claim 1, in which the complex is the iron (II) complex of N-iminodiacetic acid ethyl N'-fluorescenyl thiourea.
11. The method according to claim 1, wherein the complex is used, for the identification of consensus motifs in protein kinases.
12. The method according to any one of claims 1 to 10 wherein the complex is used in an assay and/or for the separation of compounds.
13. The method according to claim 12 which includes an analysis or separation of peptides or proteins that have identical, almost identical or different sequences, the peptides or proteins having different numbers of phosphoric ester groups.
14. The method according to claim 12 which includes an analysis or separation of peptides or proteins that have an identical or similar number of phosphoric ester groups but different sequences.
15. The method according to claim 12 which includes an analysis or separation carries out in the protein gels, on blots or by means of capillary electrophoresis.

* * * * *